United States Patent
Barbier et al.

(10) Patent No.: US 11,096,936 B2
(45) Date of Patent: Aug. 24, 2021

(54) COCRYSTALS OF NALOXONE AND NALTREXONE

(71) Applicant: PAIN THERAPEUTICS, INC., Austin, TX (US)

(72) Inventors: Remi Barbier, Austin, TX (US); Nadav Friedmann, Georgetown, TX (US); Vijay Srirambhatla, Scotland (GB); Stephen Watt, Scotland (GB); Michael Zamloot, Austin, TX (US)

(73) Assignee: Cassava Sciences, Inc., Austin, TX (US)

( * ) Notice: Subject to any disclaimer, the term of this patent is extended or adjusted under 35 U.S.C. 154(b) by 0 days.

(21) Appl. No.: 15/762,234

(22) PCT Filed: Sep. 26, 2016

(86) PCT No.: PCT/US2016/053695
§ 371 (c)(1),
(2) Date: Mar. 22, 2018

(87) PCT Pub. No.: WO2017/053936
PCT Pub. Date: Mar. 30, 2017

(65) Prior Publication Data
US 2018/0263973 A1 Sep. 20, 2018

Related U.S. Application Data

(60) Provisional application No. 62/222,920, filed on Sep. 24, 2015.

(51) Int. Cl.
| | | |
|---|---|---|
| *A61K 31/485* | (2006.01) |
| *A61K 9/70* | (2006.01) |
| *A61K 9/14* | (2006.01) |
| *A61K 31/495* | (2006.01) |
| *A61K 31/635* | (2006.01) |
| *A61K 31/60* | (2006.01) |
| *A61K 31/465* | (2006.01) |
| *A61K 9/00* | (2006.01) |
| *A61K 31/4468* | (2006.01) |
| *C07C 35/12* | (2006.01) |
| *C07C 65/05* | (2006.01) |
| *C07C 65/10* | (2006.01) |
| *C07D 213/81* | (2006.01) |

(Continued)

(52) U.S. Cl.
CPC .......... *A61K 31/485* (2013.01); *A61K 9/0014* (2013.01); *A61K 9/14* (2013.01); *A61K 9/7038* (2013.01); *A61K 9/7084* (2013.01); *A61K 31/4468* (2013.01); *A61K 31/465* (2013.01); *A61K 31/495* (2013.01); *A61K 31/60* (2013.01); *A61K 31/635* (2013.01); *C07C 35/12* (2013.01); *C07C 65/05* (2013.01); *C07C 65/10* (2013.01); *C07D 213/81* (2013.01); *C07D 239/54* (2013.01); *C07D 489/08* (2013.01); *C07C 2601/14* (2017.05)

(58) Field of Classification Search
CPC .. A61K 31/485; A61K 9/7038; A61K 9/7084; A61K 9/14; A61K 31/495; A61K 31/635; A61K 31/60; A61K 31/465; A61K 9/0014; A61K 31/4468; C07C 35/12; C07C 65/05; C07C 65/10; C07C 2601/14; C07D 213/81; C07D 239/54; C07D 489/08

See application file for complete search history.

(56) References Cited

U.S. PATENT DOCUMENTS

| 2005/0095279 A1 | 5/2005 | Gale et al. |
| 2005/0181041 A1* | 8/2005 | Goldman ............... A61K 9/145 |
| | | 424/456 |

(Continued)

FOREIGN PATENT DOCUMENTS

| EP | 2123626 A1 | 11/2009 |
| WO | 2004/078163 A2 | 9/2004 |

OTHER PUBLICATIONS

Eun Hee Lee, A Practical Guide to Pharmaceutical Polymorph Screening & Selection, 9 Asian J Pharma. Sci. 163 (Year: 2014).*
International Search Report and Written Opinion in International Application No. PCT/US2016/053695, dated Dec. 23, 2016.
International Preliminary Report on Patentability in International Application No. PCT/US2016/053695, dated Apr. 5, 2018.

*Primary Examiner* — Sean M Basquill
(74) *Attorney, Agent, or Firm* — J.A. Lindeman & Co. PLLC

(57) ABSTRACT

This invention relates to cocrystals of naloxone and of naltrexone and their use as opioid antagonists. The cocrystals of the invention include naloxone isonicotinamide cocrystal, naloxone hydrochloride piperazine cocrystal, naltrexone menthol cocrystal, naltrexone thymine cocrystal, naltrexone 2,5-dihydroxybenzoic acid cocrystal, naltrexone salicylic acid cocrystal, naltrexone hydrochloride piperazine cocrystal and naltrexone hydrochloride sulfathiazole cocrystal. A drug-in¬ adhesive transdermal patch containing the opioid analgesic fentanyl or an analog thereof and a cocrystal of naloxone or naltrexone is disclosed. Also disclosed is a method of treating pain, such as acute, chronic or intermittent pain, by applying a drug-in-adhesive transdermal patch of the invention to the skin of a patient in need thereof. Also disclosed is an improved transdermal patch for administering fentanyl or an analog thereof, or for administering a mu opioid agonist, the improvement wherein the transdermal patch contains a cocrystal of the invention in an abuse limiting amount. The improved transdermal patch may be a drug-in-adhesive transdermal patch or a reservoir transdermal patch.

16 Claims, 11 Drawing Sheets

(51) Int. Cl.
*C07D 239/54* (2006.01)
*C07D 489/08* (2006.01)

(56) References Cited

U.S. PATENT DOCUMENTS

2008/0233178 A1    9/2008   Reidenberg et al.
2016/0081946 A1    3/2016   Barbier et al.

\* cited by examiner

XRPD PATTERN OF NALOXONE HYDROCHLORIDE PIPERAZINE COCRYSTAL

TG/DTA OF NALOXONE HYDROCHLORIDE PIPERAZINE COCRYSTAL

XRPD PATTERN OF NALTREXONE MENTHOL COCRYSTAL

TG/DTA OF NALTREXONE MENTHOL COCRYSTAL

DSC THERMOGRAM OF THE NALTREXONE MENTHOL COCRYSTAL

XRPD PATTERN OF NALTREXONE THYMINE COCRYSTAL

TG/DT ANALYSIS OF NALTREXONE THYMINE COCRYSTAL

XRPD PATTERN OF NALTREXONE 2,5-DIHYDROXYBENZOIC ACID COCRYSTAL

TG/DTA TRACES FOR THE NALTREXONE 2,5-DIHYDROXYBENZOIC ACID COCRYSTAL

XRPD PATTERN OF THE NALTREXONE SALICYLIC ACID COCRYSTAL

TG/DTA TRACES FOR NALTREXONE SALICYLLIC ACID COCRYSTAL

XRPD PATTERN OF THE NALTREXONE SALICYLIC ACID COCRYSTAL FROM 1,4-DIOXANE

XRPD PATTERN OF NALTREXONE HYDROCHLORIDE PIPERAZINE COCRYSTAL FROM METHANOL

TG/DTA TRACES FOR NALTREXONE HYDROCHLORIDE PIPERAZINE COCRYSTAL FROM METHANOL

XRPD PATTERN OF THE NALTREXONE HYDROCHLORIDE SULFATHIAZOLE COCRYSTAL

TG/DTA TRACES FOR THE NALTREXONE HYDROCHLORIDE SULFATHIAZOLE COCRYSTAL

COCRYSTALS OF NALOXONE AND NALTREXONE

CROSS-REFERENCE TO RELATED APPLICATIONS

This application claims priority to U.S. application No. 62/222,920, filed Sep. 24, 2015; the disclosure of which is incorporated herein by reference.

FIELD OF THE INVENTION

This invention relates to cocrystals of naloxone and naltrexone and their use as opioid antagonists. The invention also relates to a transdermal patch, such as a drug-in-adhesive transdermal patch, containing an analgesic such as fentanyl, which is a mu opioid agonist, or an analog of fentanyl or another mu opioid agonist; and a cocrystal of naloxone or of naltrexone. The invention also relates to methods for treating pain.

BACKGROUND OF THE INVENTION

Fentanyl is a synthetic opioid analgesic used to treat moderate to severe chronic pain. Fentanyl, whose chemical name is chemical name is N-Phenyl-N-(1-(2-phenylethyl)-4-piperidinyl) propanamide, has the following chemical formula:

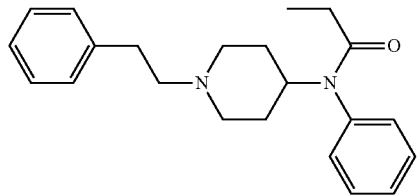 [SMILES: CCC(=O)N(c1ccccc1)C1CCN(CCc2ccccc2)CC1]

Fentanyl and its congeners, sufentanil, alfenanil and remifentanil, all act as opioid agonists mainly on mu-receptors that are present along the central nervous system. Mu-binding sites are present in the human brain, spinal cord, and other tissues that are integral to the transmission of pain pathways. Therapeutic use of intravenous fentanyl results in a rapid onset but a short duration of action, making this route of administration a popular choice as an anesthetic adjuvant. Fentanyl's low molecular weight, high potency and lipid solubility also makes it suitable for transdermal delivery. The development of transdermal fentanyl, a less invasive route of administration compared to intravenous delivery, has facilitated the use of fentanyl to manage chronic pain. Transdermal fentanyl patches such as the DURAGESIC® fentanyl transdermal system sold by Janssen Pharmaceuticals, adhere to skin and provide a prolonged, continuous, slow and therapeutic dose of fentanyl for up to 72 hours.

As with all potent mu opioid analgesics, fentanyl is also abused for its intense euphoric effects. Abusers seek rapid drug absorption. To get high, abusers often cut a small piece of the fentanyl patch and swallow it or suck on it. These actions provide abusers with a rapidly absorbed, high blood level of fentanyl, resulting in euphoric effects. Non-medicinal use of transdermal fentanyl patches is extremely dangerous and can result opioid addiction, overdose or death. Even after a 72 hour usage interval some residual fentanyl remains in the transdermal patch. Unused or used fentanyl patches are therefore also susceptible to unintentional misuse, such as accidental exposure to a transdermal fentanyl patch by children or family pets.

Methods or paradigms of abusing fentanyl transdermal patches include, for example, single or multistep extraction, physical tampering with subsequent extraction and direct administration by oral routes such as swallowing or inhaling (e.g. smoking) as well as sublingual or buccal administration, chewing and administration as a suppository. Documented methods of abusing fentanyl patches include injecting fentanyl extracted from a patch intravenously, chewing or swallowing patches, inserting patches into the rectum, inhaling fentanyl gel, and extracting fentanyl in tea. The biological effects of fentanyl are similar to those of street heroin but hundreds of times more potent. It is extremely difficult to stop its absorption because fentanyl is highly lipophilic and penetrates the central nervous system easily. Therefore, the illicit use of fentanyl is very dangerous and causes numerous opioid overdose deaths. See, W. Guan, et al., Prim Care Companion CNS Disord. 2011, 13(5) (citations omitted); http://www.ncbi.nlm.nih.gov/pmc/articles/PMC3267509/ (accessed Aug. 10, 2014).

Curtailing the misuse and abuse of fentanyl and other opioid analgesics is a difficult problem. Several approaches have been tried: formulation technologies aimed at introduction of functional characteristics that deter or resist physical and chemical practices that facilitate the non-medical use of the narcotics by various routes of administration. Such formulation technologies may impart one or more of the following abuse-deterrent characteristics to the narcotic drug product: tamper resistant secondary packaging; fabrication with crush or tear resistance laminate component seven, extraction resistance, formulation with prodrugs of the narcotic active ingredient, agonist and antagonist combinations, and even nasal gels. For a discussion of these approaches, see U.S. Pat. No. 8,338,444 B1. While the prodrug approach modifies the drug itself, the other approaches look, at least to some extent, to formulation techniques.

Formulating or placing an opioid antagonist within the opioid agonist product is the basis of the agonist/antagonist approach to curtail misuse and abuse. If the opioid agonist product is misused or there is an attempt to extract the opioid agonist from the product, the opioid antagonist is released to decrease or even block the pharmacologic effect of the opioid agonist. U.S. Pat. Nos. 8,440,220 B2 and 8,747,889 B2 disclose an analgesic system for transdermal delivery of fentanyl and analogs thereof for analgesic purposes, to a subject through intact skin over an extended period of time. The disclosure of U.S. Pat. Nos. 8,440,220 B2 and 8,747,889 B2 are incorporated herein by reference. The transdermal analgesic system is reported to have reduced potential for abuse and a substantially minimized/negligible skin sensitization response from antagonist exposure. The transdermal analgesic system is intended to provide for the controlled release of the antagonist at a rate sufficient to provide an abuse limiting release rate ratio of the antagonist to the analgesic when the dosage form is subject to abuse. In this regard, the transdermal analgesic system is intended to provide release of the antagonist at a rate sufficient to block the opioid effects of the analgesic during abuse situations. The analgesic and antagonist layers are contained in distinct reservoir layers separated by an impermeable barrier layer. The transdermal analgesic system disclosed in U.S. Pat. Nos. 8,440,220 B2 and 8,747,889 B2, however, is not a preferred solution to potential abuse employing an antagonist reservoir and an antagonist release controlling means to modulate the ingress of water/solvent to the antagonist reservoir, to modulate the release of the antagonist during abuse while permitting the release of an antagonist at a rate to limit abuse. The transdermal analgesic system is thus complex in its formulation and in its manufacture.

In view of the existing and potential abuse and misuse of fentanyl transdermal patches there remains a need in the art to develop a fentanyl transdermal patch system which mitigates, neutralizes or prevents the effects of fentanyl when a transdermal patch is intentionally abused or accidentally misused. This invention answers that need using a novel opioid analgesic/antagonist combination.

SUMMARY OF THE INVENTION

In one embodiment this invention relates to cocrystals of naloxone and of naltrexone and their use as opioid antagonists. The cocrystals of the invention include naloxone isonicotinamide cocrystal, naloxone Hydrochloride piperazine cocrystal, naltrexone menthol cocrystal, naltrexone thymine cocrystal, naltrexone 2,5-dihydroxybenzoic acid cocrystal, naltrexone salicylic acid cocrystal, naltrexone hydrochloride piperazine cocrystal and naltrexone hydrochloride sulfathiazole cocrystal.

In another embodiment the invention also relates to a drug-in-adhesive transdermal patch containing the opioid analgesic fentanyl or an analog thereof and a cocrystal of naloxone or naltrexone.

In another embodiment the invention also relates to a drug-in-adhesive transdermal patch containing a mu opioid agonist, such as fentanyl—disclosed here as a particular example, and a cocrystal of naloxone or naltrexone or mixtures thereof, as an opioid antagonist.

Another embodiment of the invention relates to a method of treating pain, such as acute, chronic or intermittent pain, by applying a drug-in-adhesive transdermal patch according to the invention to the skin of a patient in need thereof.

BRIEF DESCRIPTION OF THE FIGS

DETAILED DESCRIPTION

Figure 1:
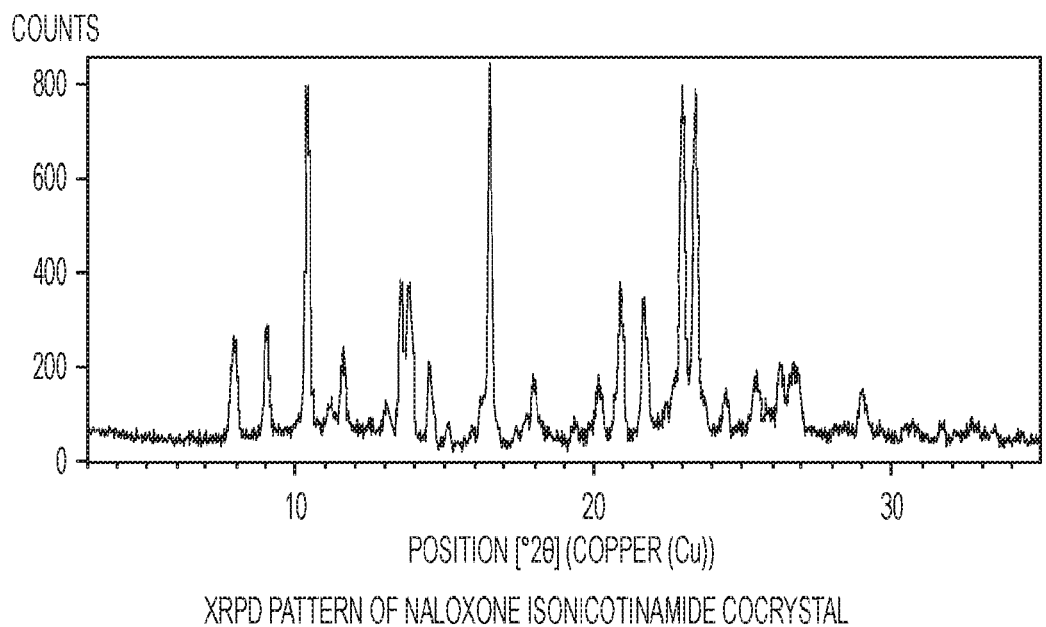
FIG. 1 depicts the experimental XRPD pattern of the naloxone isonicotinamide cocrystal prepared in Example 1.1.

Naloxone, 17-allyl-4,5α-epoxy-3,14-dihydroxymorphinan-6-one, is an opioid receptor antagonist, having the following chemical structure:

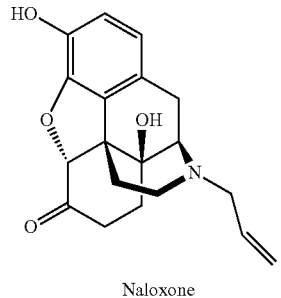

Naloxone

Naltrexone, 17-(cyclopropylmethyl)-4,5α-epoxy-3,14-dihydroxymorphinan-6-one, is an opioid receptor antagonist, having the chemical structure shown below.

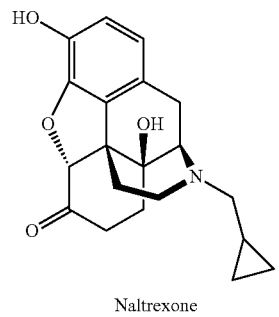

Naltrexone

Pharmaceutical uses of naltrexone as an active pharmaceutical ingredient (API) include management of alcohol dependence, opioid overdose and opioid dependence. Pharmaceutical uses of naloxone as an active pharmaceutical ingredient (API) include opioid overdose and opioid dependence. U.S. Pat. Nos. 8,440,220 B2 and 8,747,889 B2 disclose naltrexone and naloxone as an opioid antagonist used in their transdermal system.

In one embodiment this invention relates to cocrystals of naloxone and of naltrexone and their use as an opioid antagonist. In a given cocrystal of the invention, the naloxone or naltrexone may be present as its free base form or as a hydrochloride salt. It is well-known that crystalline materials obtain their fundamental physical properties from the molecular arrangement within the solid, and altering the placement and/or interactions between these molecules can, and usually does, have a direct impact on the properties of the particular solid. See, Schultheiss and Newman, "Pharmaceutical Cocrystals and Their Physiochemical Properties", *Crystal Growth & Design*, Vol. 9, No. 6, 2950-2967 (2009). Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates, permeability, hydrophilic or lipophilic character (important factors in determining drug delivery). Because these practical physical properties are influenced by the solid state properties of the crystalline form of the API, they can provide advantages for the pharmaceutical utility and formulation of the API.

Obtaining crystalline forms of an API is extremely useful in pharmaceutical development as it may affect the in vivo disposition of the active moiety, affect the rate or extent of its release from the dosage form or even enable its suitability for a particular dosage form design. It also may permit better characterization of the API's chemical and physical properties. It is also possible to achieve desired properties of a particular API by forming a cocrystal of the API and a coformer. Crystalline forms often have better chemical and physical properties than the free base in its amorphous state. Another potentially important solid state property of an API is its dissolution rate in aqueous fluids or in polymeric preparations used to formulate the API. Such crystalline forms may, as with the cocrystals of the invention, possess more favourable pharmaceutical and formulation properties or be easier to process than known forms of the API itself.

This invention relates to cocrystals of naloxone and of naltrexone, as described in the examples below. The cocrystals of the invention include naloxone isonicotinamide cocrystal, naloxone hydrochloride piperazine cocrystal, naltrexone menthol cocrystal, naltrexone thymine cocrystal, naltrexone 2,5-dihydroxybenzoic acid cocrystal, naltrexone salicylic acid cocrystal, naltrexone hydrochloride piperazine cocrystal and naltrexone hydrochloride sulfathiazole cocrystal. A cocrystal of an API, such as naloxone or naltrexone, is a distinct chemical composition of the API and coformer (s) and generally possesses distinct crystallographic and spectroscopic properties when compared to those of naloxone, naltrexone and a particular cocrystal coformer former individually. Crystallographic and spectroscopic properties of crystalline forms are typically measured by X-ray powder diffraction (XRPD) among other techniques. Cocrystals often also exhibit distinct thermal behavior. Thermal behavior is measured in the laboratory by such techniques as capillary melting point, thermogravimetric analysis (TGA) and differential scanning calorimetry (DSC). The cocrystals of the invention and the methods used to characterize them are described in the examples below.

Figure 2:
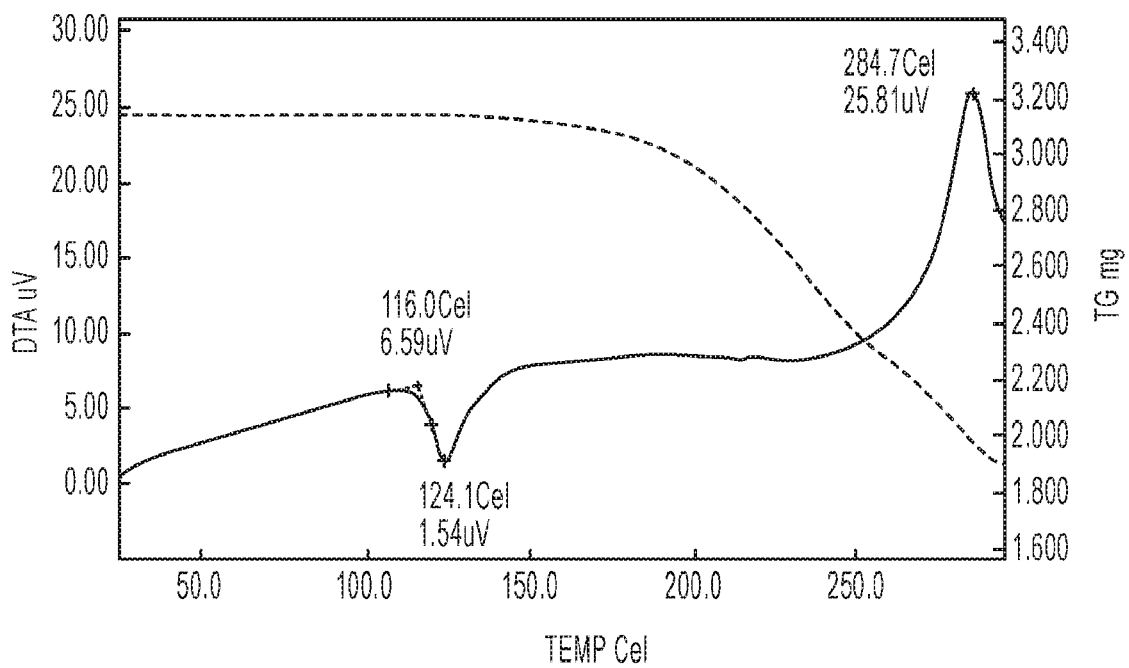
FIG. 2 depicts the TG/DTA traces for the naloxone isonicotinamide cocrystal prepared in Example 1.1.
Figure 3:
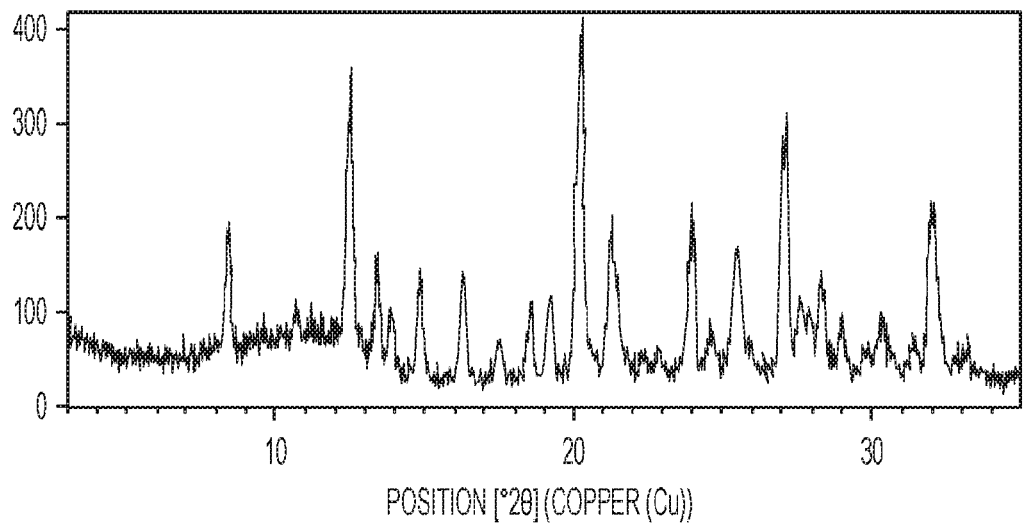
FIG. 3 depicts the experimental XRPD pattern of the naloxone hydrochloride piperazine cocrystal prepared in Example 2.1.
Figure 4:
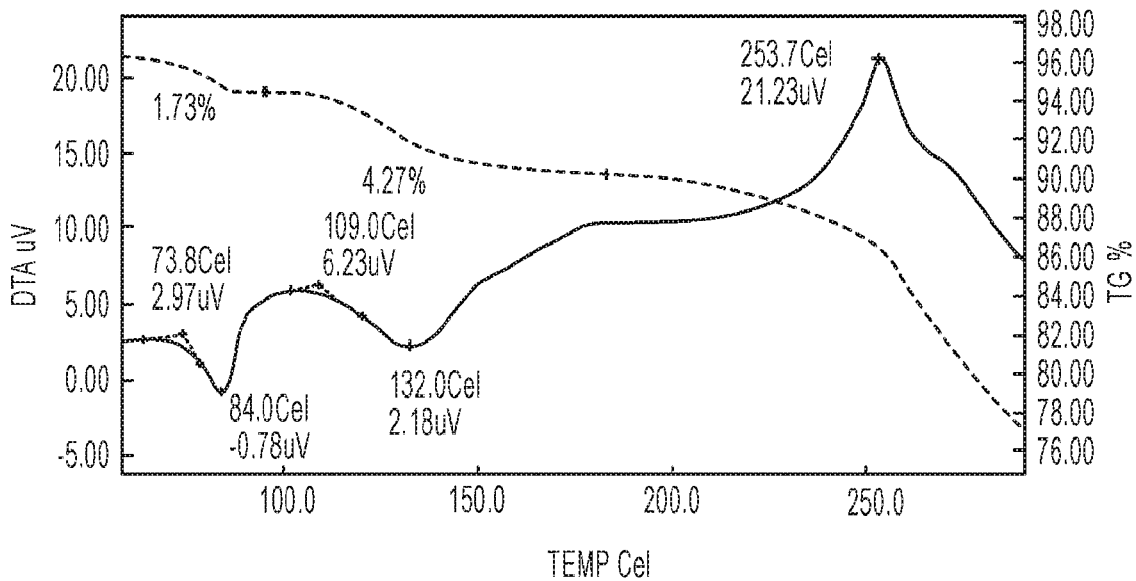
FIG. 4 depicts the TG/DTA traces for the naloxone hydrochloride piperazine cocrystal prepared in Example 2.1.
Figure 5:
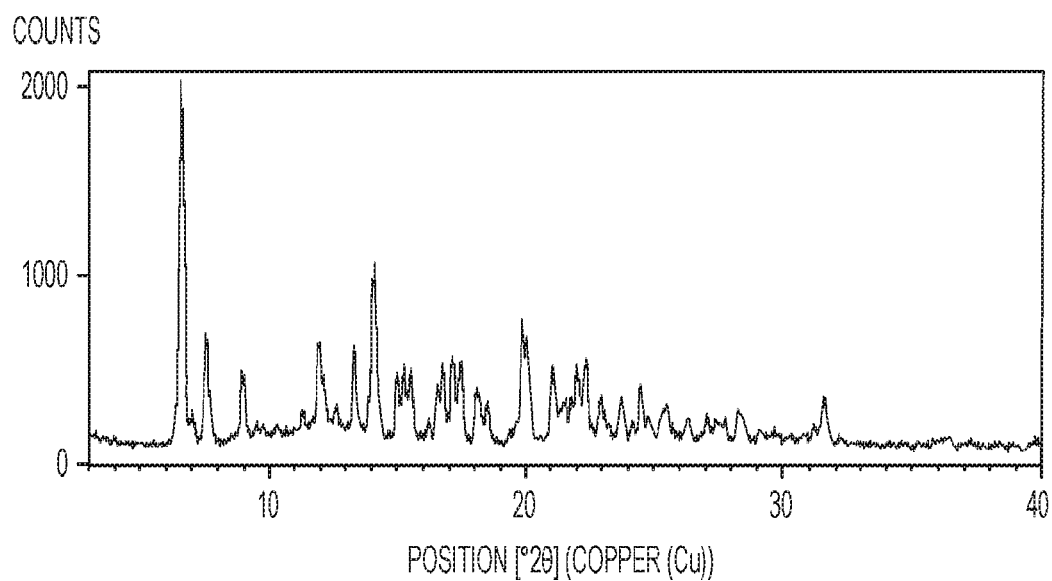
FIG. 5 depicts the experimental XRPD pattern of the naltrexone menthol cocrystal prepared in Example 3.1.
Figure 6:
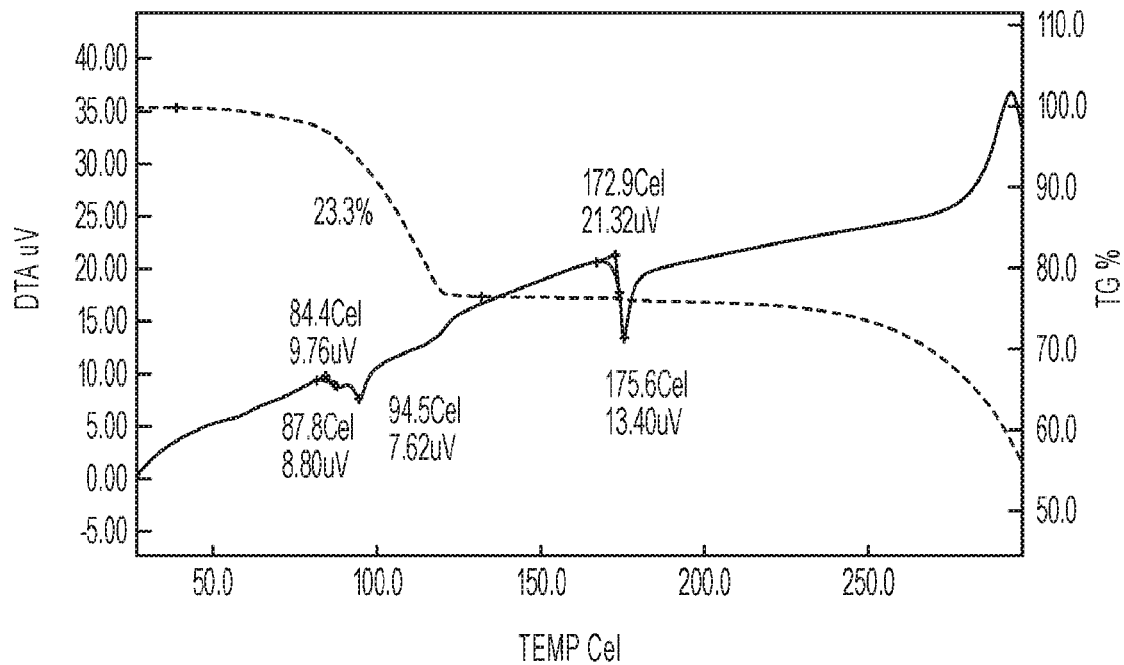
FIG. 6 depicts the TG/DTA traces for the naltrexone menthol cocrystal prepared in Example 3.1.
Figure 7:
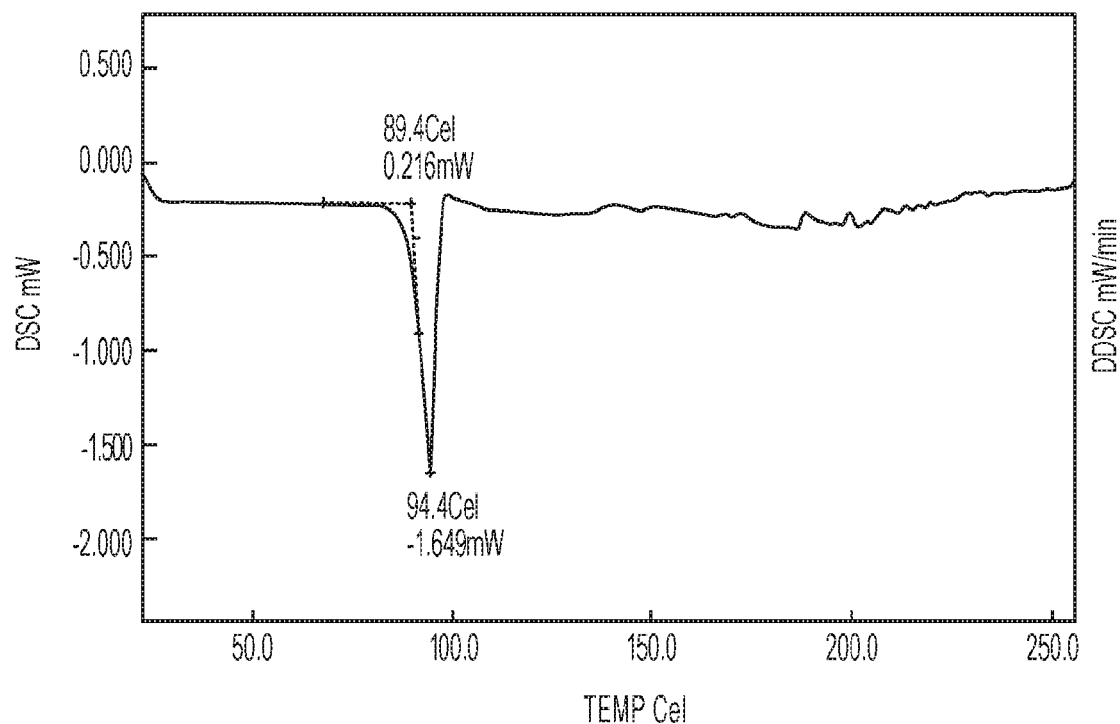
FIG. 7 depicts the DSC thermogram of the naltrexone menthol cocrystal prepared in Example 3.1.
Figure 8:
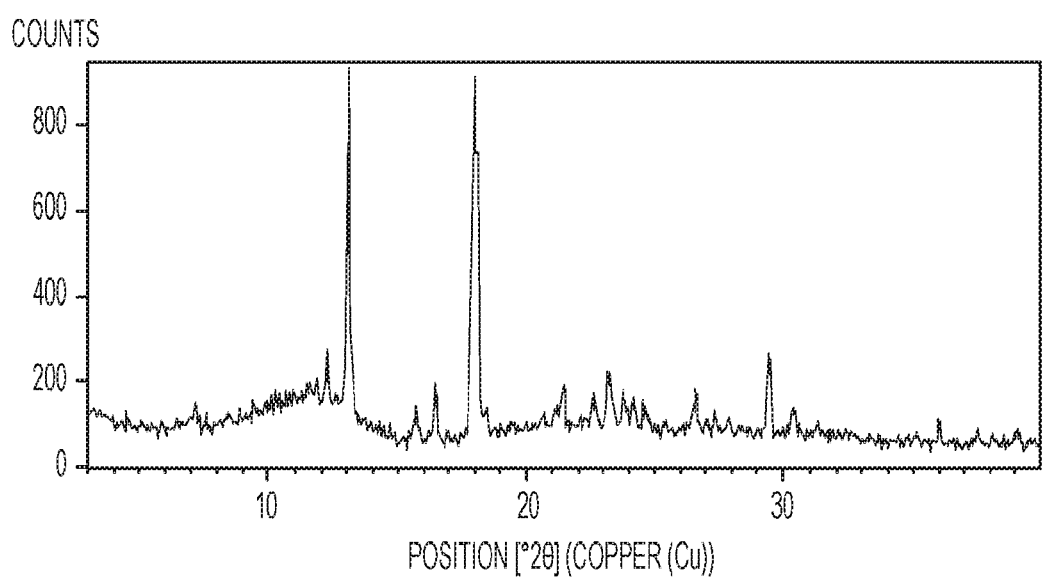
FIG. 8 depicts the experimental XRPD pattern of the naltrexone thymine cocrystal prepared in Example 4.1.
Figure 9:
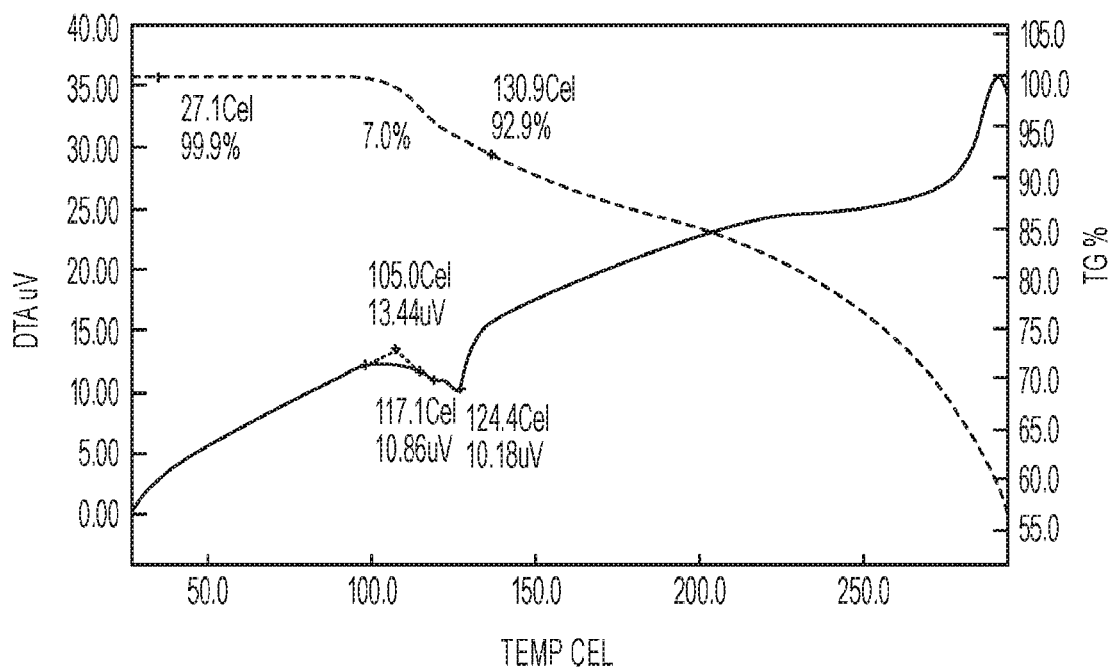
FIG. 9 depicts the TG/DTA traces of the naltrexone thymine cocrystal prepared in Example 4.1.
Figure 10:
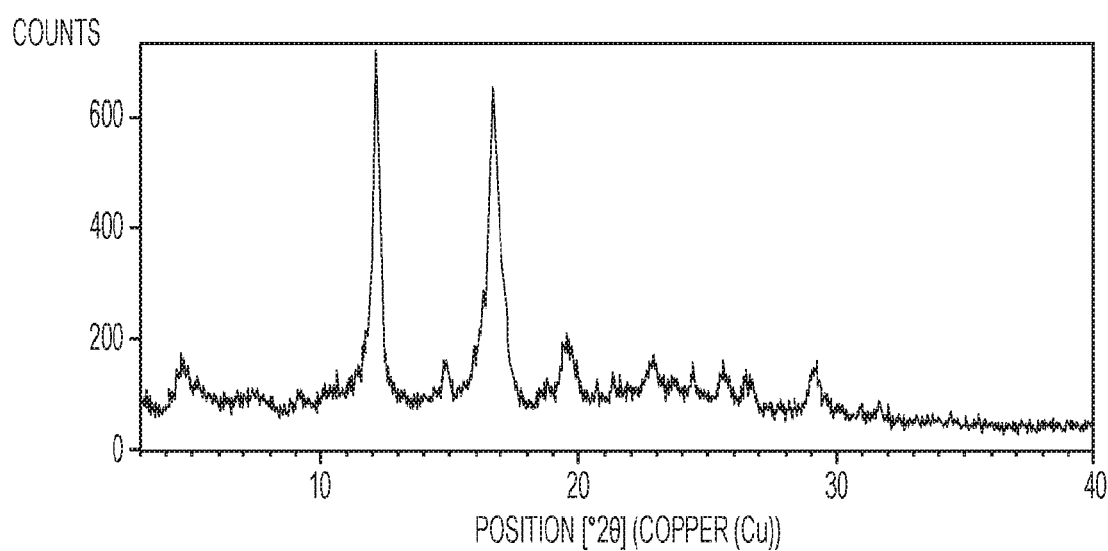
FIG. 10 depicts the experimental XRPD pattern of the naltrexone 2,5-dihydroxybenzoic acid cocrystal prepared in Example 5.1.
Figure 11:
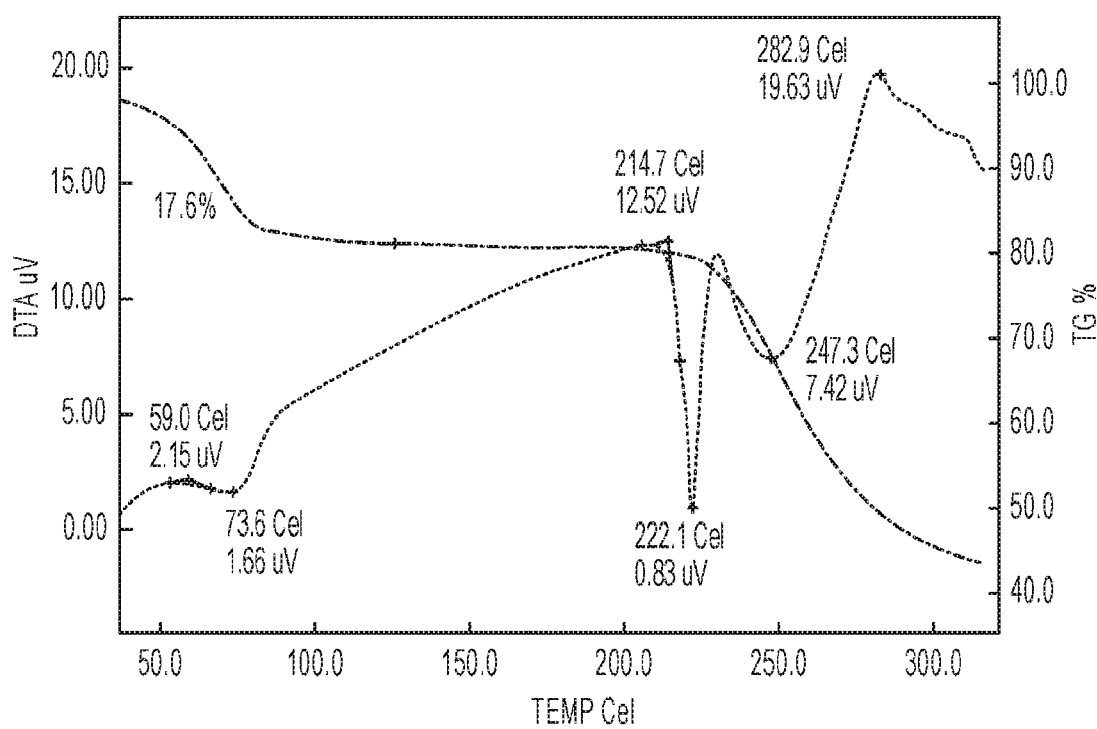
FIG. 11 depicts the TG/DTA traces for the naltrexone 2,5-dihydroxybenzoic acid cocrystal prepared in Example 5.1.
Figure 12:
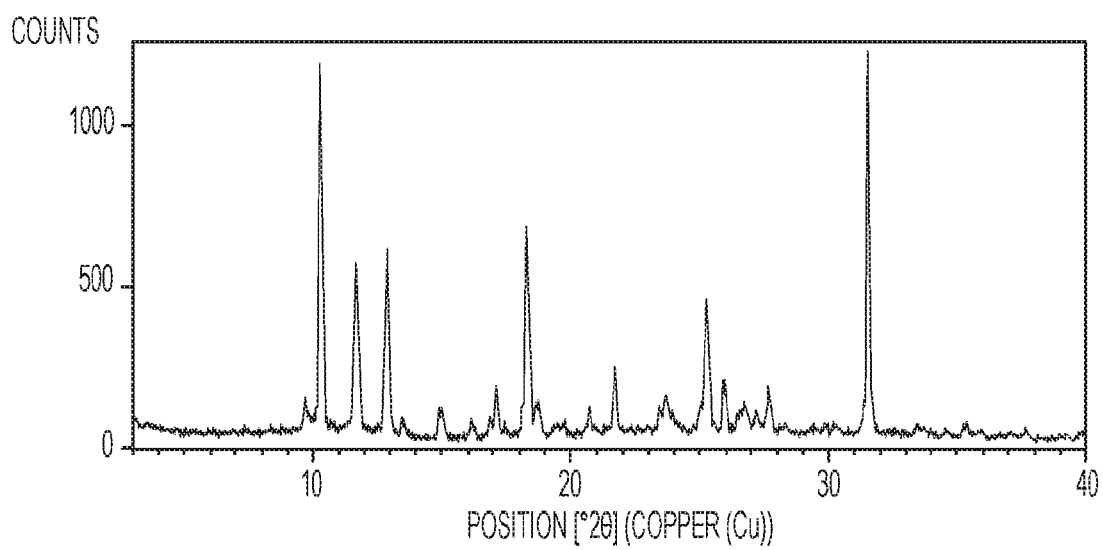
FIG. 12 depicts the XRPD pattern of the naltrexone salicylic acid cocrystal prepared in Example 6.1.
Figure 13:
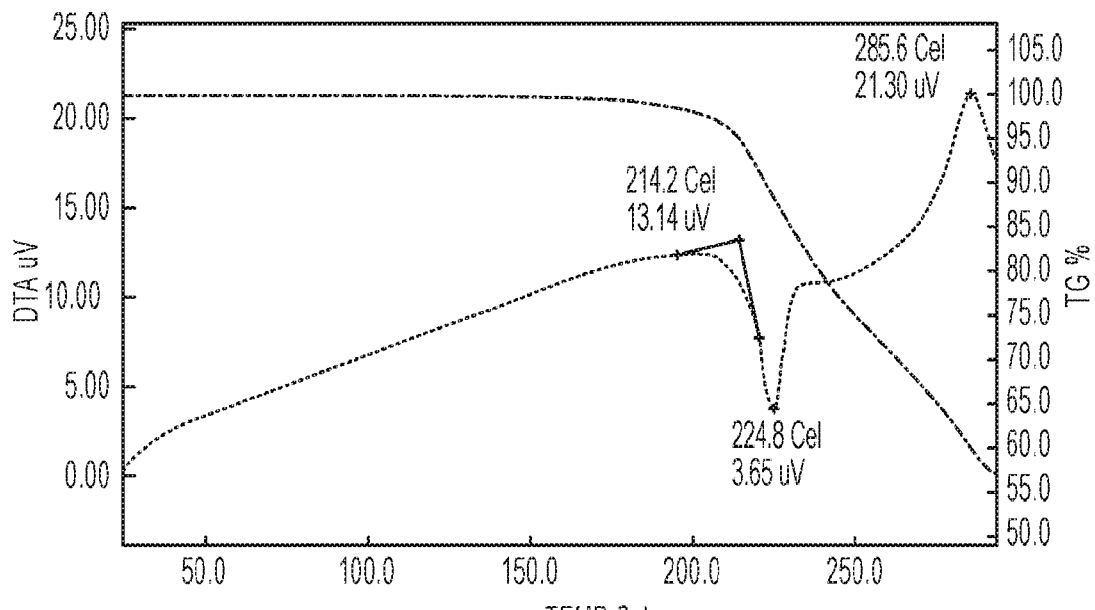
FIG. 13 depicts the TG/DTA traces for the naltrexone salicylic acid cocrystal prepared in Example 6.1.
Figure 14:
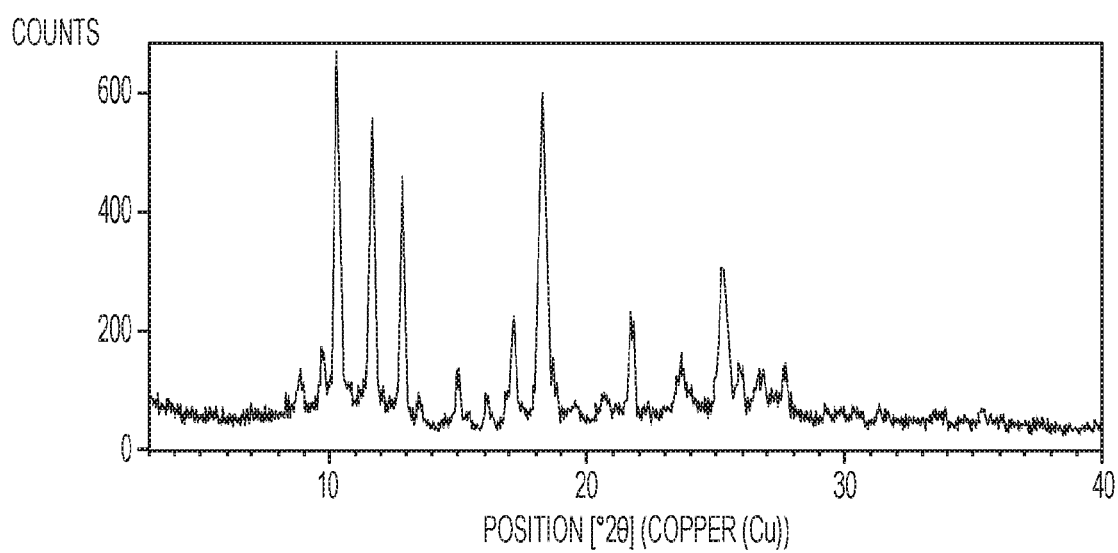
FIG. 14 depicts the experimental XRPD pattern of the naltrexone salicylic acid cocrystal from 1,4-dioxane prepared in Example 6.4
Figure 15:
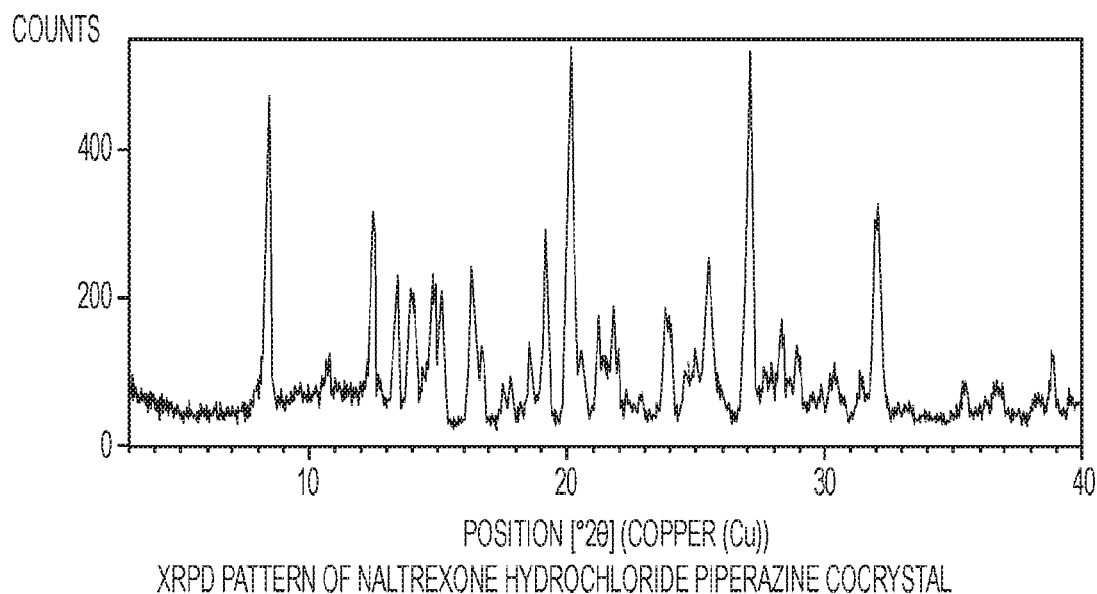
FIG. 15 depicts the experimental XRPD pattern of the naltrexone hydrochloride piperazine cocrystal from acetone prepared in Example 7.1.
Figure 16:
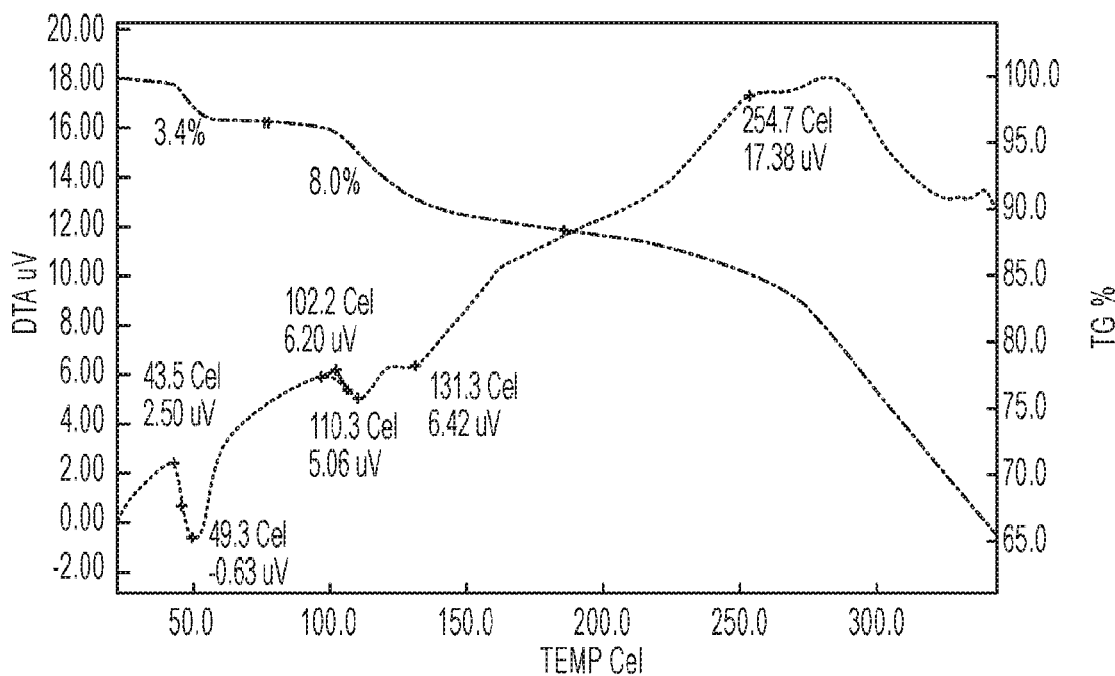
FIG. 16 depicts the TG/DTA traces for the naltrexone hydrochloride piperazine cocrystal from acetone prepared in Example 7.1.
Figure 17:
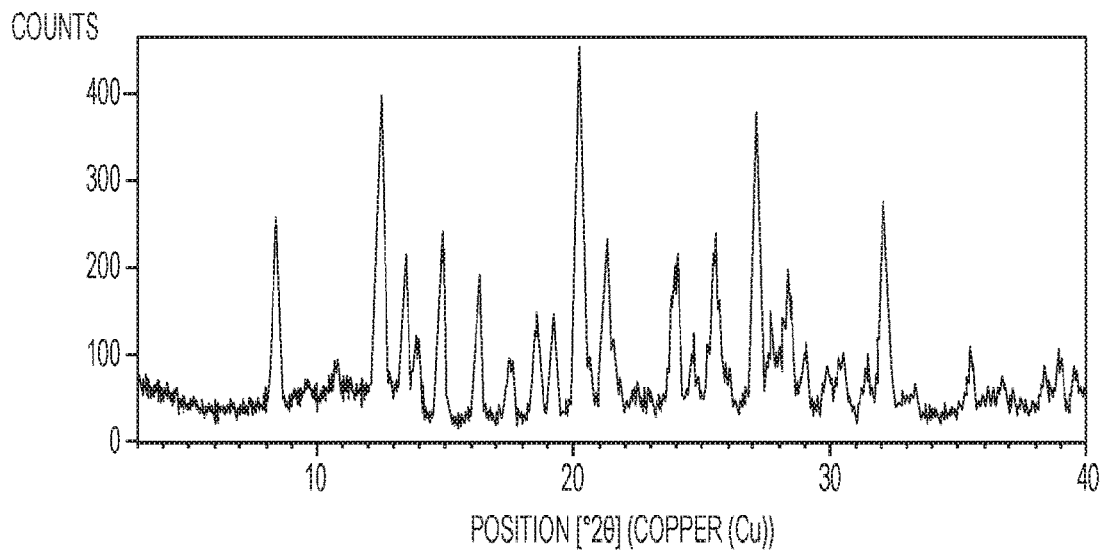
FIG. 17 depicts the experimental XRPD pattern of the naltrexone hydrochloride piperazine cocrystal from methanol prepared in Example 7.4.
Figure 18:
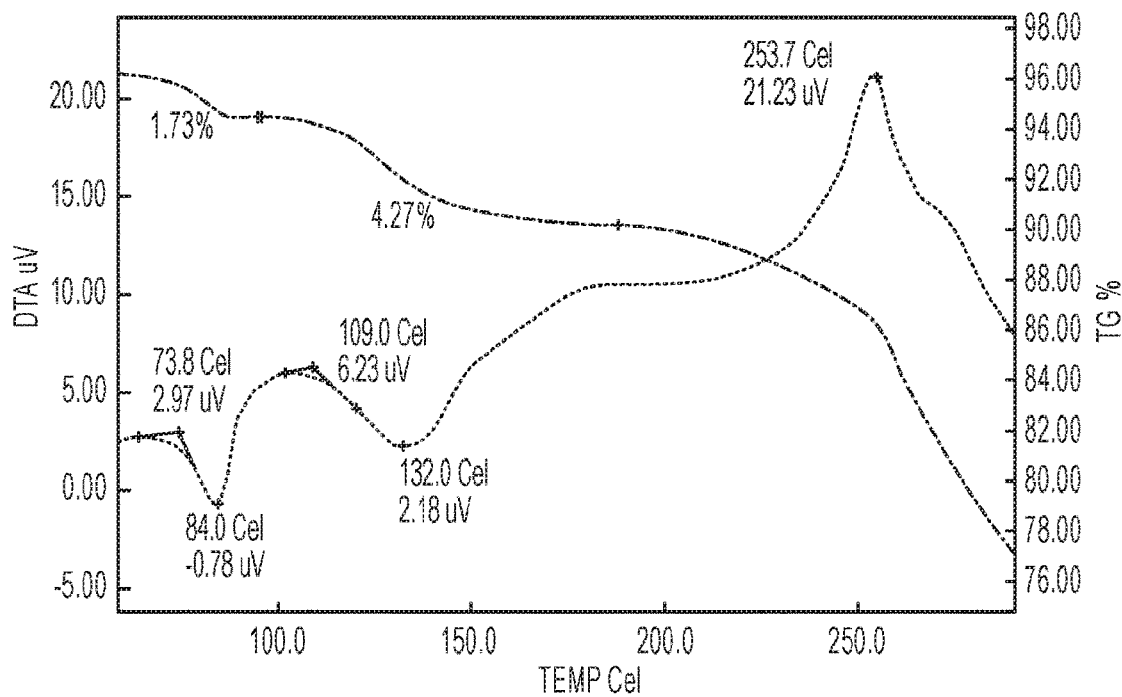
FIG. 18 depicts the TG/DTA traces for the naltrexone hydrochloride piperazine cocrystal from methanol prepared in Example 7.4.
Figure 19:
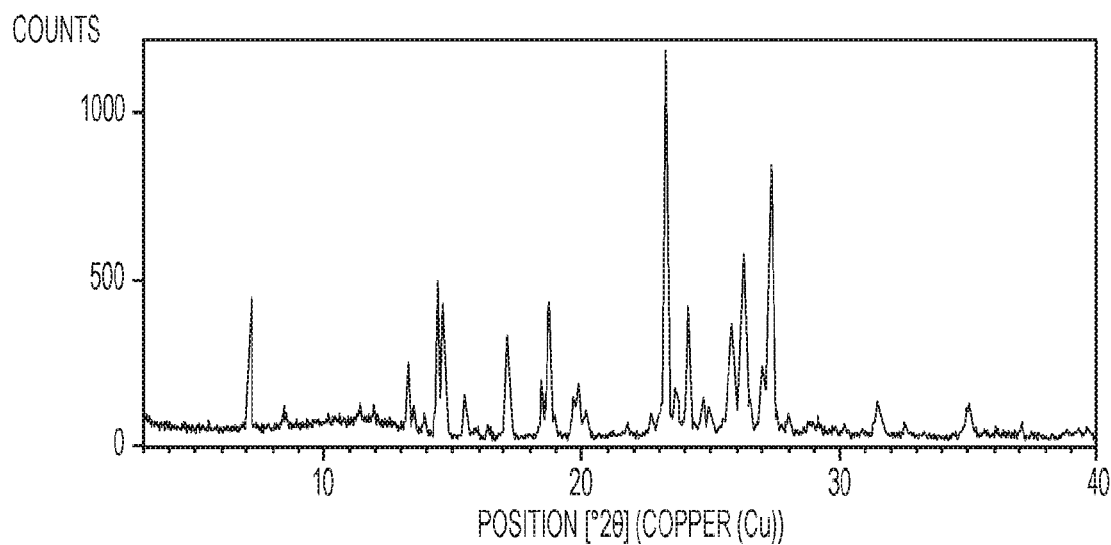
FIG. 19 depicts the experimental XRPD pattern of the naltrexone hydrochloride sulfathiazole cocrystal prepared in Example 8.1.
Figure 20:
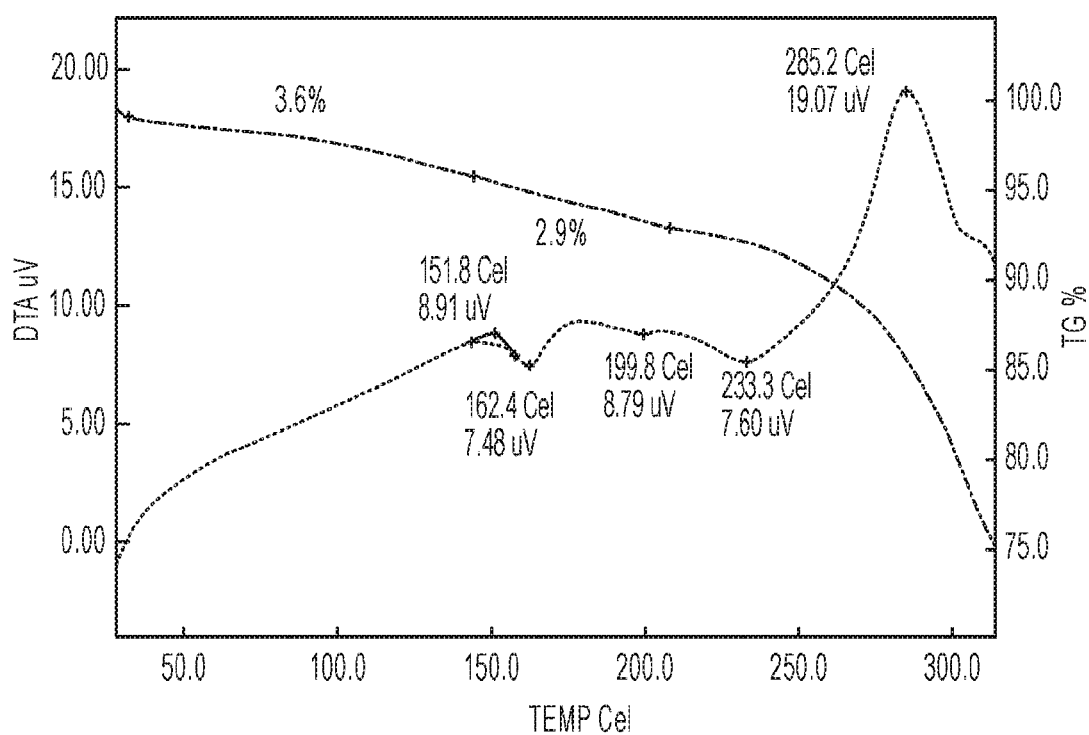
FIG. 20 depicts the TG/DTA traces for the naltrexone hydrochloride sulfathiazole cocrystal prepared in Example 8.1.

As separate embodiments, the invention also relates to cocrystals of the invention selected from the group consisting of:

a naloxone isonicotinamide cocrystal characterized by an XRPD pattern as shown in FIG. 1 or a TG/DTA trace as shown in FIG. 2;

a naloxone hydrochloride piperazine cocrystal characterized by an XRPD pattern as shown in FIG. 3 or a TG/DTA trace as shown in FIG. 4 a naltrexone menthol cocrystal characterized by an XRPD pattern as shown in FIG. 5, a TG/DTA trace as shown in FIG. 6, or a DSC thermogram as shown in FIG. 7;

a naltrexone thymine cocrystal characterized by an XRPD pattern as shown in FIG. 8 or a TG/DTA trace as shown in FIG. 9;

a naltrexone 2,5-dihydroxybenzoic acid characterized by an XRPD pattern as shown in FIG. 10 or a TG/DTA trace as shown in FIG. 11;

a naltrexone salicylic acid cocrystal characterized by an XRPD pattern as shown in FIG. 12 or in FIG. 14, or a TG/DTA trace as shown in FIG. 13;

a naltrexone hydrochloride piperazine cocrystal characterized by an XRPD pattern as shown in FIG. 15 or in FIG. 17, or a TG/DTA trace as shown in FIG. 16 or in FIG. 18;

a naltrexone hydrochloride sulfathiazole cocrystal characterized by an XRPD pattern as shown in FIG. 19 or a TG/DTA trace as shown in FIG. 20.

In another embodiment, the invention relates to a drug-in-adhesive transdermal patch (also known as a monolithic transdermal patch) containing the analgesic fentanyl, a mu opioid agonist, or an analog thereof and cocrystals of naloxone and of naltrexone or mixtures thereof, as an opioid antagonist. This provides a tamper-resistant or an abuse-deterrent transdermal fentanyl patch. The opioid agonist analgesic may be fentanyl or an analog thereof such as, but not limited to, alfentanil, lofentanil, remifentanil, sufentanil and trefentanil. Fentanyl is a preferred opioid analgesic. Another embodiment of the invention relates to a drug-in-adhesive transdermal patch containing a mu opioid agonist and a cocrystal of naloxone and of naltrexone of the invention as an opioid antagonist. Combinations of cocrystals of naloxone and of naltrexone may also be used as the opioid antagonist.

A drug-in-adhesive transdermal patch contains the drug to be delivered in an adhesive polymer matrix. The adhesive polymer matrix contains the drug, and a pressure sensitive adhesive (PSA) comprised of one or more polymers suitable for adhesion to the skin. The adhesive polymer matrix and its method of preparation should be selected such that it is compatible with fentanyl or the fentanyl analog used and such that the crystalline form of the cocrystal of naloxone and of naltrexone used is maintained. Examples of pressure sensitive adhesives include, but are not limited to, silicones/polysiloxanes polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylene/butylene-styrene copolymers (SEBS), and di-block analogs thereof. These adhesive polymers are soluble in low polarity solvents and the matrix of the transdermal patch may be prepared by mixing the drug and cocrystal into the polymer solution followed by solvent casting of the matrix layer. Alternatively, a melt blending process in which the polymer is heated to achieve a sufficiently low viscosity to allow dry mixing of the drug and cocrystal may be employed. If the adhesive polymer matrix is formed by the melt blending and extrusion process, then polyacrylates and ethylene/vinyl acetate copolymers may be used in the adhesive polymer matrix in addition to the rubber-based adhesive polymers. Silicones are a preferred type of PSA polymers used in a drug-in-adhesive transdermal patch of the invention. Amine-compatible silicones PSA's, such as Dow Corning BioPSA 7-4101, are compatible with fentanyl free base and may be used in fentanyl-containing adhesive layers for that reason. Silicone PSAs have a low saturation solubility for fentanyl and its analogs. This allows for a zero order delivery rate of fentanyl while undissolved drug is present and after 72 hours less fentanyl remains in the patch, most having been delivered to the patient.

To prepare a drug-in-adhesive transdermal patch, the drug to be delivered, for example fentanyl or a fentanyl derivative, may first be dispersed in an oil and then the dispersion mixed into the adhesive polymer as is known the art. See, for example, U.S. Pat. No. 4,559,222, which is incorporated herein by reference. The cocrystal of naloxone and of naltrexone used may also be dispersed as particles in the oil as long as the cocrystal is not soluble or only sparingly soluble in the oil. Depending on the drug to be delivered and the adhesive polymer to be used, mineral oil or a silicone oil are common choices when considering PSA compatibility. The dispersion is mixed into the adhesive polymer using known blending techniques and at a shear rate is not so high as to break up the adhesive polymer. As mentioned, silicone PSA's are a preferred type of adhesive for a drug-in-adhesive transdermal patch of the invention. An example of a silicone oil is Dow-Corning 360 Medical Fluid, a linear polydimethylsiloxane (PDMS) which is available in several different viscosities. Dow-Corning 360 Medical Fluid having a viscosity of 100 cSt is a preferred silicone oil.

Figure 21:
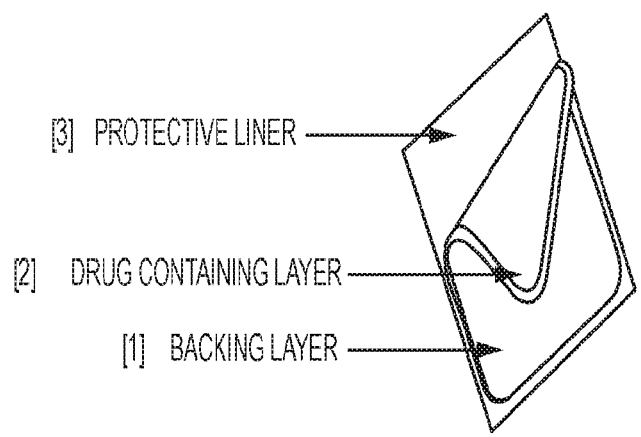
FIG. 21 depicts a drug-in-adhesive transdermal patch.

An example of a drug-in-adhesive transdermal patch used to deliver fentanyl is the DURAGESIC® fentanyl transdermal system sold by Janssen Pharmaceuticals. In the DURAGESIC® transdermal system the amount of fentanyl released from each system per hour is proportional to the surface area (25 mcg/h per 10.5 cm$^2$). The composition per unit area of all system sizes is identical. The DURAGESIC® transdermal system, shown in FIG. 21, is a rectangular transparent unit comprising a protective liner and two functional layers. Proceeding from the outer surface toward the surface adhering to skin, these layers are: a backing layer [1] composed of polyester/ethyl vinyl acetate film; and a drug-in-adhesive layer [2]. Before use, a protective liner (release sheet) [3] covering the adhesive layer is removed and discarded. See, DURAGESIC® US prescribing information, http://www.duragesic.com/sites/default/files/pdf/duragesic 0.pdf, (accessed Aug. 11, 2014). Other drug-in-adhesive transdermal patch structures and variations are known in the art.

In a drug-in-adhesive transdermal patch of the invention, particles of a cocrystal of naloxone or of naltrexone are present in the drug-in-adhesive layer as a dispersion of solid particles along with the fentanyl or an analog thereof. In an embodiment of the invention, the drug-in-adhesive layer is a monolithic layer. As known in the art, fentanyl itself is solubilized in the adhesive polymer(s) making up the drug-in-adhesive layer or present as a molecular dispersion. The cocrystal of naloxone or of naltrexone is substantially or completely insoluble in the adhesive polymer(s), a solubility for the cocrystal of naloxone or of naltrexone of about 0 wt % to about 1 wt % of the total adhesive polymer composition. The relative solubility of the fentanyl and insolubility of the cocrystal of naloxone or of naltrexone provide a rate control mechanism allowing the fentanyl to be delivered to the skin and the cocrystal of naloxone or naltrexone to be retained in the drug-in-adhesive layer. The particles of a cocrystal of naloxone or of naltrexone are typically distributed as a dispersed powder throughout the drug-in-adhesive layer to provide a uniform composition per unit area.

A cocrystal of naloxone or of naltrexone may be soluble in water, aqueous media certain organic solvents and mixed aqueous-organic systems; however, its insolubility in the drug-in-adhesive layer does not permit its release in any substantial or therapeutic amount in response to the moisture which may be present at the skin surface during use of the transdermal patch. The drug-in-adhesive transdermal patch of the invention, however, does release naloxone or naltrexone that dissociates from the coformer or anion present in the cocrystal at a rate and in an amount sufficient to provide an abuse limiting dose of the opioid antagonist to the opioid analgesic when subjected to non-medical use or accidental misuse. Thus, a drug-in-adhesive transdermal patch of the invention releases naltrexone which is the dissociation product of cocrystal of naloxone or of naltrexone as a result of the exposure to elevated temperature (i.e., a smoking paradigm of abuse) or an aqueous environment, (e.g. water or other aqueous extraction solution or saliva depending on the paradigm of abuse), and provides sufficient naltrexone to decrease or block the pharmacologic effects of the opioid during abuse or misuse situations. A transdermal patch of the invention is therapeutically equivalent to a fentanyl-only patch when the patch is administered according to prescriptive practice for a legitimate medical purpose. When the patch is misused, abused or administered inconsistently with prescribed practice, e.g., swallowed, extracted, chewed, sucked on, smoked, etc., a transdermal patch of the invention will deliver partially or fully antagonizing dose of naltrexone which imparts safety from fentanyl or opioid analgesic over-dose, which can result in death, and will reduce the rewarding effect, i.e., a "drug-liking" or euphoric effect, that is craved by drug abusers. In this way, a transdermal patch of the invention provides sufficient release of naltrexone to reduce or eliminate "drug-liking" or euphoric effects of the abuse and offers a margin of safety resulting from full or partial antagonism of fentanyl. Advantageously, a transdermal patch of the invention provides a margin of safety against abuse but also against overdose and even death.

The drug-in-adhesive layer may contain about 0.05 to about 1.75 mg/cm$^2$ of fentanyl or an analog thereof; preferably about 0.07 to about 1.50 mg/cm$^2$ of fentanyl or an analog thereof; about 0.08 to about 1.25 mg/cm$^2$ of fentanyl or an analog thereof; about 0.09 to about 1.0 mg/cm$^2$ of fentanyl or an analog thereof; about 0.1 to about 0.75 mg/cm$^2$ of fentanyl or an analog thereof; or about 0.12 to about 0.5 mg/cm$^2$ of fentanyl or an analog thereof. For other mu opioid agonists the drug-in-adhesive layer may contain the same or similar amounts appropriate for the particular agonist as known in the art. The amount of a cocrystal of naloxone or of naltrexone present in the drug-in-adhesive layer is an amount sufficient to at least reduce the "drug liking" impact of the drug abuse and/or to provide a partial or full blockade of the analgesic effect. The amount of cocrystal of naloxone or of naltrexone present in terms of the molar ratio of naltrexone to fentanyl or an analog thereof, or other mu opioid agonist used, may range from about 0.075:1 to about 30:1, about 0.25:1 to about 20:1, about 0.5:1 to about 16:1, about 0.5:1 to about 14:1, about 0.75:1 to about 12:1, about 1:1 to about 10:1, about 1.5:1 to about 8:1, about 2:1 to about 6:1, and about 2:1 to about 4:1.

As discussed above, the adhesive used in the drug-in-adhesive layer may be a standard pressure sensitive adhesives known in the art or mixtures thereof. The adhesive polymer matrix and its method of preparation should be selected such that it is compatible with fentanyl or the fentanyl analog used and such that the crystalline form of the cocrystal of naloxone or of naltrexone used is maintained. The adhesive polymer matrix is formulated to control the release of the drug from the patch and its permeation through the skin. As known in the art, the adhesive polymer matrix may also contain plasticizers or tackifiers that modify the rheology and adhesion characteristics of the adhesive, and may additionally include a chemical permeation enhancer such as alcohols, fatty acids and esters to modify the rate of drug penetration through the skin. The drug-in-adhesive layer may optionally contain additional components such as, additives, stabilizers, dyes, diluents, pigments, carriers, inert fillers, antioxidants, excipients, gelling agents, anti-irritants, vasoconstrictors and other materials as are generally known to the transdermal art.

A drug-in-adhesive transdermal patch of the invention may be manufactured using methods known in the art. The cocrystal of naloxone or of naltrexone particles may be incorporated into the drug-in-adhesive layer also using known methods such as melt blending. The cocrystal of naloxone or of naltrexone particles may be dispersed in a liquid in which the cocrystal is not soluble or only sparingly soluble (a "non-solvent" and then added to a solution of the other drug-in-adhesive layer components in that same liquid. Alternatively, the cocrystal of naloxone or of naltrexone particles may be dispersed into the solution of the drug-in-adhesive components itself. Use of a non-solvent ensures that the cocrystal retains its crystalline form while forming the drug-in-adhesive layer. For a cocrystal of naloxone or of naltrexone such a liquid will generally be a non-polar organic solvent, such as, for example, heptane and the like. Alternatively, the cocrystal of naloxone or of naltrexone particles may be incorporated into the drug-in-adhesive layer also using known methods such as melt blending.

The invention further relates to a method of treating pain, such as acute, chronic or intermittent pain, by applying a drug-in-adhesive transdermal patch according to the invention to the skin of a patient in need thereof. Accordingly the invention relates to the use of a drug-in-adhesive transdermal patch to treat pain in a patient in need thereof. Patients should apply a transdermal patch of the invention to intact, non-irritated, and non-irradiated skin on a flat surface such as the chest, back, flank, or upper arm. A transdermal patch of the invention is typically worn for up to 72 hours.

As discussed above, transdermal patches are used in the art to administer fentanyl or an analog thereof to treat pain as well as to administer other mu opioid agonists. Transdermal patches, generally speaking, are either a drug-in-adhesive style (discussed above) or a reservoir style. In a reservoir style transdermal patch, the drug to be delivered is contained in a reservoir portion with a membrane between placed between the drug reservoir and the skin. The membrane controls the release rate of drug to the skin. As known in the art, a reservoir-style transdermal patch typically has a backing layer, a drug reservoir portion, a membrane, an adhesive and a release sheet, which is removed from the patch to expose the adhesive when applying the patch to the skin. The transdermal analgesic system disclosed in U.S. Pat. Nos. 8,440,220 B2 and 8,747,889 B2, discussed above, are examples of reservoir style transdermal patches. In those reservoir transdermal patches the analgesic and antagonist layers are contained in distinct reservoir layers separated by an impermeable barrier layer and the antagonist is to release only is situations of misuse or abuse.

In another embodiment, the invention relates to an improvement in transdermal patches used to administer fentanyl or an analog thereof or another mu opioid agonist. The invention combines in a transdermal patch an effective amount of a naloxone cocrystal, a naltrexone cocrystal of the invention or a mixture of those cocrystals as an opioid antagonist to provide a tamper-resistant or abuse-deterrent transdermal patch. Accordingly, the invention relates to an improved transdermal patch for administering fentanyl or an analog thereof, or for administering a mu opioid agonist, the improvement wherein the transdermal patch contains a naloxone and/or a naltrexone cocrystal in an abuse limiting amount such as those amounts discussed above. The improved transdermal patch may any transdermal patch type known in the art, including but not limited to a drug-in-adhesive transdermal patch or a reservoir transdermal patch.

EXAMPLES

The following analytical methods were used to characterize the cocrystal of naloxone or of naltrexons of the invention. In the examples, room temperature is identified as 22° C.

X-Ray Powder Diffraction (XRPD) Characterization:

XRPD analysis was carried out on a Siemens D5000, scanning the samples between 3 and 30.0° 2θ. The material was gently compressed onto a glass disc inserted into an XRPD sample holder. The sample was then loaded into a Siemens D5000 diffractometer running in reflection mode and analysed, using the experimental conditions described in Table 1.

TABLE 1

| | |
|---|---|
| Raw Data Origin | Siemens-binary V2 (.RAW) |
| Start Position [°2θ] | 3.0 |
| End Position [°2θ] | 35.0 |
| Step Size [°2θ] | 0.020 |
| Scan Step Time [s] | 1 |
| Scan Type | Continuous |
| Offset [°2θ] | 0.0 |
| Divergence Slit Type | Fixed |
| Divergence Slit Size [mm] | 2.0 |
| Specimen Length [mm] | Various |
| Receiving Slit Size [mm] | 0.20 |
| Measurement Temperature [° C.] | 20.0 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50 (nominal) |
| Generator Settings | 40 mA, 40 kV |
| Diffractometer Type | D5000 |
| Goniometer Radius [mm] | 217.50 |
| Incident Beam Monochromator | No |
| Diffracted Beam Monochromator | (Graphite) |
| Spinning | No |

Thermogravimetric/Differential Thermal Analysis (TG/DTA):

Approximately, 10 mg of material was weighed into an open aluminium pan and loaded into a simultaneous thermogravimetric/differential thermal analyser (Seiko TG/DTA 620) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm³/min.

Differential Scanning Calorimetry (DSC):

Approximately 5 mg of material was weighed into an aluminium DSC pan and sealed nonhermetically with a pierced aluminium lid. The sample pan was then loaded into a Seiko DSC6200 (equipped with a cooler) cooled and held at 25° C. Once a stable heat-flow response was obtained, the sample and reference were heated to 220° C. at scan rate of 10° C./min and the resulting heat flow response monitored.

Example 1: Naloxone Isonicotinamide Cocrystal 1.1 Preparation of Naloxone Isonicotinamide Cocrystal 16.3 mg of naloxone (0.050 mmoles) were dissolved in 300 µl of methanol. 6.1 mg of isonicotinamide (0.050 mmoles) were dissolved in 200 µl of methanol. The two solutions were mixed together and left to evaporate. Crystals of naloxone isonicotinamide cocrystal were collected after the evaporation of the solvent.

1.2 XRPD Characterisation of Naloxone Isonicotinamide Cocrystal

The experimental XRPD pattern of the naloxone isonicotinamide cocrystal is shown in FIG. 1.

1.3 TG/DTA of Naloxone Isonicotinamide Cocrystal

FIG. 2 shows the TG/DTA analysis of the naloxone isonicotinamide cocrystal. The DTA curve shows a sharp endothermic transition at 124.1° C. with an onset of 116.0° C., likely to be the melt of the cocrystal. This is followed by a broad exotherm associated with loss of weight starting around 200° C., which corresponds to the decomposition of the material.

Example 2: Naloxone Hydrochloride Piperazine Cocrystal 2.1 Preparation of Naloxone Hydrochloride Piperazine Cocrystal 20 mg of naloxone hydrochloride dihydrate (0.050 mmoles) and 4.30 mg of piperazine (0.050 mmoles) were ground with a mortar and pestle in presence of 100 µl of methanol. Subsequently to this grinding a dry powder of the naloxone hydrochloride piperazine cocrystal was obtained.

2.2 XRPD Characterization of Naloxone Hydrochloride Piperazine Cocrystal

The experimental XRPD pattern of the naloxone hydrochloride piperazine cocrystal is shown in FIG. 3.

2.3 TG/DTA of Naloxone Hydrochloride Piperazine Cocrystal

FIG. 4 shows the TG/DTA analysis of naloxone hydrochloride piperazine cocrystal. The DTA curve of the material shows an endothermic transition at 84.0° C. with an onset of 73.8° C., which corresponds to a weight loss of 1.73%. This transition is followed by a broad endothermic transition at 132° C., with a corresponding weight loss of 4.27%. This is followed by exothermic event with the peak occurring at 253.7° C. which is the decomposition of the material.

Example 3: Naltrexone Menthol Cocrystal 3.1 Preparation of Naltrexone Menthol Cocrystal 81.58 mg of naltrexone freebase monohydrate (0.227 mmoles) and 22.74 mg of menthol (0.145 mmoles) were ground with a mortar and pestle in presence of 300 µl of acetonitrile. Subsequently to this grinding a dry powder of the Naltrexone menthol cocrystal was obtained.

3.2 XRPD Characterization of Naltrexone Menthol Cocrystal

The experimental XRPD pattern of the naltrexone menthol cocrystal is shown in FIG. 5.

3.3 TG/DTA Analysis of Naltrexone Menthol Cocrystal

The TG/DTA analysis of naltrexone menthol cocrystal is shown in FIG. 6. The TG data suggests that there is an initial weight loss of 23.3%, with an onset temp of 84.4° C. The weight loss in the TGA corresponds to the loss of 0.62 moles of menthol. It is followed by the melting of the remaining material with an onset temp of 172.9° C.

3.4 DSC Analysis of Naltrexone Menthol Cocrystal

Shown in FIG. 7 the DSC thermogram of naltrexone menthol cocrystal shows one endotherm with an onset at 89.4° C.

Example 4: Naltrexone Thymine Cocrystal 4.1 Preparation of Naltrexone Thymine Cocrystal 17.8 mg of naltrexone freebase monohydrate (0.05 mmoles) and 6.49 mg of thymine (0.051 mmoles) were ground with a mortar and pestle in presence of 200 µl of propan-2-ol and 100 µl of DMSO. Subsequently to this grinding a dry powder of the Naltrexone thymine cocrystal was obtained.

41 XRPD Characterization of Naltrexone Thymine Cocrystal

The experimental XRPD pattern of the Naltrexone thymine cocrystal is shown in FIG. 8.

4.3 TG/DTA of Naltrexone Thymine Cocrystal

FIG. 9 shows the TG/DTA analysis of naltrexone thymine cocrystal. The TG/DTA data of potential cocrystal phase suggests that there is an initial weight loss of 7.0% between 80-130.9° C. This corresponds to the loss of 0.37 moles of DMSO or 0.46 moles of 2-propanol from the crystal lattice. The weight loss in the TG curve is seen as an endotherm in the DTA followed by endothermic transition corresponding to the melting of the compound at 124.4° C.

Example 5: Naltrexone 2,5-dihydroxybenzoic Acid Cocrystal 5.1 Preparation of Naltrexone 2,5-dihydroxybenzoic Acid Cocrystal by Evaporation at 22° C.

17.075 mg of naltrexone (0.048 mmoles) were dissolved in 300 µl of 1,4-dioxane. 7.73 mg of 2,5-dihydroxybenzoic acid (0.050 mmoles) were dissolved in 300 µl of 1,4-dioxane. The two solutions were mixed together and left to evaporate. Crystals of Naltrexone 2,5-dihydroxybenzoic acid cocrystal were collected after the evaporation of the solvent. Noting the pKa values of naltrexone and 2,5-dihydroxybenzoic acid, the cocrystal isolated may be a crystalline salt.

5.2 XRPD Characterization of Naltrexone 2,5-dihydroxybenzoic Acid Cocrystal from 1,4-dioxane The experimental XRPD pattern of the naltrexone 2,5-dihydroxybenzoic acid cocrystal from 1,4-dioxane is shown in FIG. 10.

5.3 TG/DTA of the Naltrexone 2,5-dihydroxybenzoic Acid Cocrystal

FIG. 11 shows the TG/DTA analysis for the naltrexone 2,5-dihydroxybenzoic acid cocrystal. The DTA curve shows a broad endotherm at 73.6° C. with a corresponding weight loss of 17.6% in the TG curve, this transition is followed by a sharp endotherm at 222.1° C. with an onset of 214.7° C. corresponding to the melting of the material. The melting transition is immediately followed by a broad endotherm at 247.3° C. and an exothermic transition occurring at 282.9° C. corresponding to decomposition of the compound.

Example 6: Naltrexone Salicylic Acid Cocrystal 6.1 Preparation of Naltrexone Salicylic Acid Cocrystal by Evaporation at 22° C.

17.110 mg of naltrexone (0.048 mmoles) were dissolved in 300 µl of propan-2-ol. 6.85 mg of salicylic acid (0.050 mmoles) were dissolved in 300 µl of propan-2-ol. The two solutions were mixed together and left to evaporate. Crystals of Naltrexone salicylic acid cocrystal were collected after the evaporation of the solvent. Noting the pKa values of naltrexone and salicylic acid, the cocrystal isolated may be a crystalline salt.

6.2 XRPD Characterization of Naltrexone Salicylic Acid Cocrystal from propan-2-ol The experimental XRPD pattern of the naltrexone salicylic acid cocrystal from propan-2-ol is shown in FIG. 12.

6.3 TG/DTA of the Naltrexone Salicylic Acid Cocrystal

FIG. 13 shows the TG/DTA analysis of the naltrexone salicylic acid cocrystal. The DTA curve shows a sharp endotherm at 224.8° C. with an onset at 214.2° C. This transition is followed by transitions corresponding to decomposition.

6.4 Preparation of Naltrexone Salicylic Acid Cocrystal from 1,4-dioxane by Evaporation at 22° C.

17.130 mg of naltrexone (0.048 mmoles) were dissolved in 300 µl of 1,4-dioxane. 6.83 mg of salicylic acid (0.050 mmoles) were dissolved in 300 µl of 1,4-dioxane. The two solutions were mixed together and left to evaporate. Crystals of Naltrexone salicylic acid cocrystal were collected after the evaporation of the solvent.

6.5 Characterization by XRPD of Naltrexone Salicylic Acid Cocrystal from 1,4-dioxane The experimental XRPD characterization the naltrexone salicylic acid cocrystal from 1,4-dioxane is shown in FIG. 14.

Example 7: Naltrexone Hydrochloride Piperazine Cocrystal 7.1 Preparation of Naltrexone Hydrochloride Piperazine Cocrystal by Solvent Drop Grinding at 22° C.

37.8 mg of naltrexone hydrochloride (0.100 mmoles) and 8.63 mg of piperazine (0.100 mmoles) were ground with a mortar and pestle in presence of 100 µl of acetone. Subsequently to this grinding a dry powder of the naltrexone hydrochloride piperazine cocrystal was obtained.

7.2 XRPD Characterization of Naltrexone Hydrochloride Piperazine Cocrystal from Acetone.

The experimental XRPD characterization of naltrexone hydrochloride piperazine cocrystal is shown in FIG. 15.

7.3 TG/DTA of the Naltrexone Hydrochloride Piperazine Cocrystal from Acetone

FIG. 16 shows the TG/DTA analysis for the naltrexone hydrochloride piperazine cocrystal The DTA data of the material shows an endothermic event at around 49.3° C. with an onset of 43.5° C., which corresponds to a weight loss of 3.4%, this event is likely to be the loss of acetone from the lattice. This is followed by two endothermic events at 110.3° C. and 131.3° C. corresponding to a combined weight loss of 8.0%. This is followed by exothermic events corresponding to the decomposition of the compound.

7.4 Preparation of Naltrexone Hydrochloride Piperazine Cocrystal by Solvent Drop Grinding in Methanol at 22° C.

37.7 mg of naltrexone hydrochloride (0.100 mmoles) and 8.60 mg of piperazine (0.100 mmoles) were ground with a mortar and pestle in presence of 100 µl of methanol. Subsequently to this grinding a dry powder of the naltrexone hydrochloride piperazine cocrystal was obtained.

7.5 XRPD Characterization of Naltrexone Hydrochloride Piperazine Cocrystal from Methanol The experimental XRPD characterization of the naltrexone hydrochloride piperazine cocrystal from methanol is shown in FIG. 17.

7.6 TG/DTA of the Naltrexone Hydrochloride Piperazine Cocrystal from Methanol

FIG. 18 is the TG/DTA analysis of the naltrexone hydrochloride piperazine cocrystal from methanol. The DTA curve of the material shows an endothermic transition at 84.0° C. with an onset of 73.8° C., which corresponds to a weight loss of 1.73%, likely to be some loss of methanol being part of the lattice. This transition is followed by a broad endothermic transition at 132° C., with a corresponding weight loss of 4.27%. This is followed by exothermic event with the peak occurring at 253.7° C. which is the decomposition of the material.

Example 8: Naltrexone Hydrochloride Sulfathiazole Cocrystal 8.1 Preparation of Naltrexone Hydrochloride Sulfathiazole Cocrystal by Solvent Drop Grinding at 22° C.

38.0 mg of naltrexone hydrochloride (0.100 mmoles) and 25.54 mg of sulfathiazole (0.100 mmoles) were ground with a mortar and pestle in presence of 100 µl of acetone. Subsequently to this grinding a dry powder of the naltrexone hydrochloride sulfathiazole cocrystal was obtained.

8.2 XRPD Characterization of Naltrexone Hydrochloride Sulfathiazole Cocrystal

The experimental XRPD characterization of the naltrexone hydrochloride sulfathiazole cocrystal is shown in FIG. 19.

8.3 TG/DTA of the Naltrexone Hydrochloride Sulfathiazole Cocrystal

FIG. 20 shows the TG/DTA analysis for the naltrexone hydrochloride sulfathiazole cocrystal. The DTA curve shows a broad endotherm at around 100° C., corresponding to a loss of 3.6% of the initial weight. This is followed by a endothermic transition at 162.4° C. with an onset of 151.6° C. This transition is immediately followed by two broad endothermic transitions followed by exothermic transition at around 285.2° C. corresponding to the decomposition of the material.

The claimed invention is:

1. A naltrexone salicylic acid cocrystal characterized by an XRPD pattern as shown in FIG. 12 or in FIG. 14, or a TG/DTA trace as show in FIG. 13.

2. A drug-in-adhesive transdermal patch comprising:
a backing layer;
an adhesive layer disposed on the backing layer, the adhesive layer comprising a pressure sensitive adhesive, an opioid agonist, and the naltrexone salicylic acid cocrystal according to claim 1; and
a release layer disposed on the adhesive layer opposite the backing layer.

3. An improved transdermal patch for administering fentanyl or an analog thereof, or for administering a mu opioid agonist, the improvement wherein the transdermal patch contains the naltrexone salicylic acid cocrystal according to claim 1 in an abuse limiting amount.

4. The improved transdermal patch according to claim 3, wherein the transdermal patch is a drug-in-adhesive transdermal patch or a reservoir transdermal patch.

5. A drug-in-adhesive transdermal patch containing an opioid agonist and the naltrexone salicylic acid cocrystal according to claim 1, as an opioid antagonist.

6. A method of treating pain by applying a drug-in-adhesive transdermal patch according to claim 2 to the skin of a patient in need thereof.

7. The method of claim 6, wherein the pain is acute, chronic, or intermittent pain.

8. A method of treating pain by applying a transdermal patch according to claim 3 to the skin of a patient in need thereof.

9. The method of claim 8, wherein the pain is acute, chronic, or intermittent pain.

10. A method of treating pain by applying a transdermal patch according to claim 4 to the skin of a patient in need thereof.

11. The method of claim 10, wherein the pain is acute, chronic, or intermittent pain.

12. A method of treating pain by applying a drug-in-adhesive transdermal patch according to claim 5 to the skin of a patient in need thereof.

13. The method of claim 12, wherein the pain is acute, chronic, or intermittent pain.

14. The naltrexone salicylic acid cocrystal according to claim 1, characterized by an XRPD pattern as shown in FIG. 12.

15. The naltrexone salicylic acid cocrystal according to claim 1, characterized by an XRPD pattern as shown in FIG. 14.

16. The naltrexone salicylic acid cocrystal according to claim 1, characterized by a TG/DTA trace as shown in FIG. 13.

* * * * *